(12) United States Patent
Jalota et al.

(10) Patent No.: US 11,241,317 B2
(45) Date of Patent: Feb. 8, 2022

(54) BONE GRAFT CONTAINMENT SYSTEM

(71) Applicant: SECADA MEDICAL LLC, Newport Beach, CA (US)

(72) Inventors: Sahil Jalota, Carlsbad, CA (US); Russell Cook, Newport Beach, CA (US)

(73) Assignee: SECADA MEDICAL LLC, Newport Beach, CA (US)

( * ) Notice: Subject to any disclaimer, the term of this patent is extended or adjusted under 35 U.S.C. 154(b) by 0 days.

(21) Appl. No.: 16/865,121

(22) Filed: May 1, 2020

(65) Prior Publication Data

US 2021/0338430 A1 Nov. 4, 2021

(51) Int. Cl.
| | |
|---|---|
| *A61F 2/00* | (2006.01) |
| *A61L 27/56* | (2006.01) |
| *A61L 27/48* | (2006.01) |
| *A61L 27/36* | (2006.01) |
| *A61L 27/24* | (2006.01) |
| *A61K 35/32* | (2015.01) |
| *A61F 2/28* | (2006.01) |
| *A61L 27/58* | (2006.01) |
| *A61F 2/44* | (2006.01) |
| *A61L 27/34* | (2006.01) |
| *A61L 27/10* | (2006.01) |
| *A61F 2/30* | (2006.01) |

(52) U.S. Cl.
CPC .......... *A61F 2/2846* (2013.01); *A61F 2/4455* (2013.01); *A61L 27/10* (2013.01); *A61L 27/34* (2013.01); *A61L 27/3608* (2013.01); *A61L 27/56* (2013.01); *A61L 27/58* (2013.01); *A61F 2002/2835* (2013.01); *A61F 2002/30062* (2013.01); *A61F 2002/30784* (2013.01); *A61F 2002/30957* (2013.01); *A61F 2310/00179* (2013.01); *A61F 2310/00371* (2013.01)

(58) Field of Classification Search
CPC .................. A61F 2/2846; A61F 2/4455; A61F 2002/2835; A61F 2002/30062; A61F 2002/30784; A61F 2002/30957; A61F 2310/00179; A61F 2310/00371; A61L 27/10; A61L 27/34; A61L 27/3608; A61L 27/56; A61L 27/5824; A61L 27/3683; A61L 27/48; A61L 2430/02
USPC ........... 623/17.11, 17.16, 23.5, 23.51, 23.56, 623/23.58, 10; 424/423, 426, 93.7; 435/177, 180, 395
See application file for complete search history.

(56) References Cited

U.S. PATENT DOCUMENTS

| | | | | |
|---|---|---|---|---|
| 4,430,760 | A * | 2/1984 | Smestad | A61F 2/2846 |
| | | | | 623/10 |
| 7,604,817 | B2 * | 10/2009 | Yi | A61L 27/58 |
| | | | | 424/423 |
| 9,011,537 | B2 * | 4/2015 | Wei | A61F 2/4603 |
| | | | | 623/16.11 |
| 9,364,583 | B2 * | 6/2016 | McKay | A61L 27/56 |
| 9,486,316 | B2 * | 11/2016 | Horton | A61B 17/707 |
| 2011/0022149 | A1 * | 1/2011 | Cox | A61B 17/12181 |
| | | | | 623/1.11 |

(Continued)

*Primary Examiner* — Pedro Philogene
(74) *Attorney, Agent, or Firm* — Brown Rudnick LLP

(57) ABSTRACT

The present invention relates to methods for bioresorbable and biodegradable casings having both micropores and macropores for providing shape, structure and containment to different bone grafting materials. Kits and methods of use are also described.

24 Claims, 7 Drawing Sheets

(56) References Cited

U.S. PATENT DOCUMENTS

| | | | | |
|---|---|---|---|---|
| 2011/0022180 A1* | 1/2011 | Melkent | ............... | B05D 1/18 |
| | | | | 623/23.5 |
| 2016/0228615 A1* | 8/2016 | Kasahara | ............ | A61L 27/18 |
| 2018/0296343 A1* | 10/2018 | Wei | ................. | B29C 64/386 |

* cited by examiner

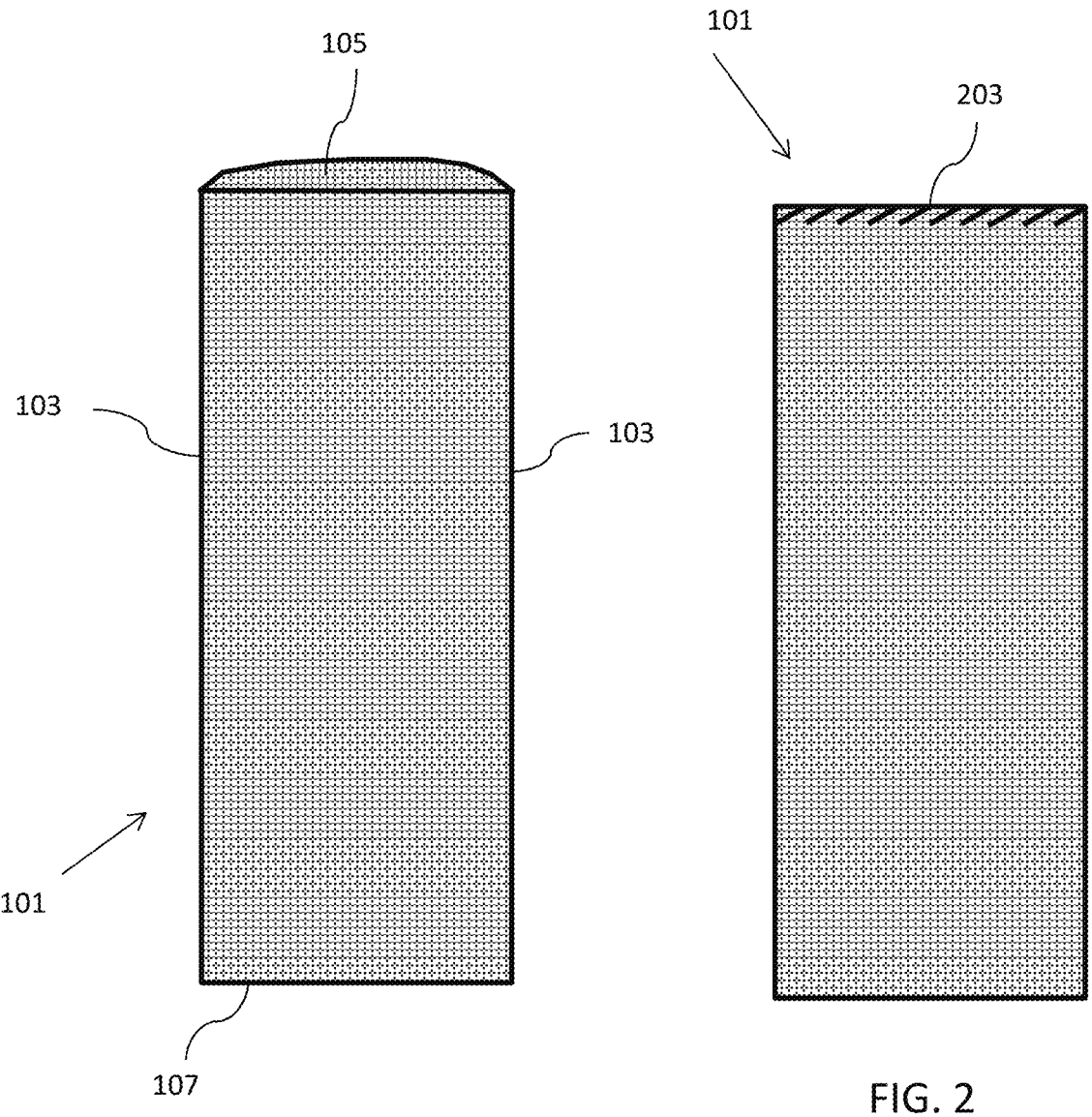

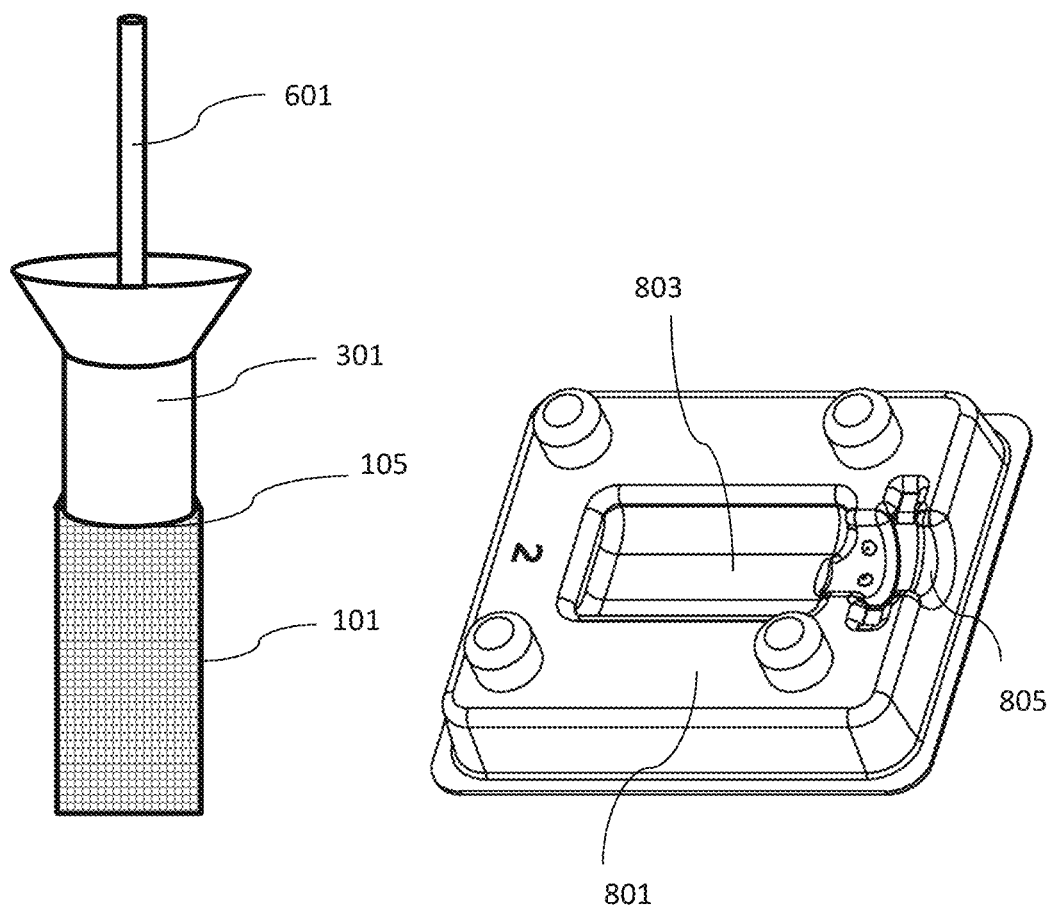

BONE GRAFT CONTAINMENT SYSTEM

FIELD OF THE INVENTION

The present disclosure generally relates to fillable collagen containers for use in bone grafting.

BACKGROUND

Artificial or synthetic bone can be used to repair damaged areas where natural regeneration may not be feasible or practical. The ability to incorporate new bone growth through osteoconductivity and osteoinductivity are important factors in artificial bone materials. Osteoconductivity is the ability to serve as a scaffold for new bone growth while osteoinductivity refers to the ability of graft material to induce de novo bone growth with biomimetic substances, such as bone morphogenetic proteins.

Recent advances in tissue engineering have produced materials such as calcium phosphates that possess both osteoconductive and osteoinductive properties, thereby, providing a suitable bone grafting material. Calcium phosphates may include hydroxyapatite (HA) or beta-tricalcium phosphate ($\beta$TCP) or biphasic calcium phosphate (a combination of HA and $\beta$TCP).

Artificial or synthetic bone, as well as demineralized bone is most commonly, and advantageously, used in particulate form as powders or granules. The particulate nature radically increases the available surface area once implanted, improving osteoinductivity. The preferred particulate nature of graft materials, however, poses a problem when trying to form larger prostheses for implantation, such as in spinal fusion procedures. The use of putties attempts to address handling issues with particulate DBM but often require a significant (about 60% in some cases) amount of carrier which dilutes the amount of DBM and therefore reduces its effectiveness.

Commercially available mesh pouches such as Ballast from SeaSpine Holdings Corporation (Carlsbad, Calif.) and Magnifuse from Medtronic plc (Ireland) have been designed to provide containment and shape to particulate bone grafting material without relying on putties with large amounts of carrier. Such pouches also allowing access for bodily fluids and osteogenic cells to the grafting material therein. Such designs attempt to retain the surface area advantages of particulate grafting materials while allowing for containment and shaping for specific prostheses and procedures. However, the materials and specifics used in the existing designs have their own shortcomings and leave room for improvement.

SUMMARY

The present invention provides bioresorbable casings having both micropores and macropores suitable for containing a variety of bone-grafting materials while allowing osteogenic cells and bodily fluids to pass through. In preferred embodiments, the casing may be constructed of collagen providing advantages over existing mesh pouches constructed from absorbable polymers such as polyglycolide (PGA) or poly (lactic-co-glycolic)acid (PLGA) in that the degraded material does not require clearance from the body. The casings may be filled with bone-grafting particles such as bioceramics, demineralized bone matrix (DBM), or combinations thereof in any form including fibers, granules, paste, powder, chips, strips, and sponge. The DBM can be obtained from cortical or cancellous bone. In certain embodiments, the bioceramics particles may include HA, tricalcium phosphate, monetite, brushite, or mono-calcium phosphate monohydrate (MCPM). Additional fill materials may include bioglass, collagen-ceramic mixtures, cell based products, autografts, and growth factor containing products.

As noted, the presence of both micropores and macropores differentiates the present casing from existing products. Those pores may be randomly distributed or may be localized in specific patterns based on intended use and orientation of the implanted casing. Pores may be generated through molding or may be generated after molding through mechanical or thermal techniques such as laser perforation. The casing may comprise nanopores.

Casings may be provided closed and pre-filled with grafting material, ready for implantation. Alternatively, the casing may be provided with an opening. The open casing may be pre-filled with some amount of grafting material or may be empty ready for filling by a technician or medical professional in advance of implantation or as part of the implantation process. Open casings may remain open or may be closed through the use of sutures, adhesives, heat, chemical treatment, pressure, folded or other means before implantation. Sutures may also be made of collagen. In certain embodiments, by providing an open casing to a surgeon, fresh autologous bone or other cells may be obtained from the patient and added to the casing at the time of implantation.

Casings may be molded or otherwise formed in a tube shape of desired size or may be formed from one or more strips of a material such as collagen. For example, a strip of collagen mesh may be folded over itself and the folded sides sutured or otherwise joined together to form a pouch.

The adaptability of the casings described herein allows them to be prepared in almost any shape and size for a variety of applications. Casings can be sized and shaped to repair patient-specific injuries or defects as modeled from radiographic or other patient imaging. Casing can be provided in standard shapes and sizes for procedures such as spinal fusion (e.g., placement in the posterolateral gutter) across two or more vertebrae.

To facilitate application-specific implantation, casing of the invention may be provided in implantable device kits. Kits may include one or more of a holder for receiving and positioning a casing for fill, a fill material, a rigid or semi-rigid fill tube to insert into the casing to facilitate filling, and a plunger to aid in loading the casing with fill. Means for closing the casing after filling such as a suture material may also be included.

The casing may be collagen or other materials as described herein. A fill tube can be sized to fit snugly into an opening in the casing to provide a stable path for fill material to be inserted. The fill tube may be in two or more portions which may be assembled by inserting one into another. The end of the fill tube that is not inserted into the casing may have a larger cross-sectional profile than the inserted end providing a funnel shape to facilitate filling. In various embodiments, the funnel portion may be separable from the inserted portion of the fill tube.

The holder may comprise a body sized and shaped similarly to the casing such that the casing can be placed in and positioned by the body. The holder may fully enclose the casing apart from an opening that is aligned with the casing's open end when the casing is positioned in the body. The holder may comprise two or more pieces including, for example, a lid so that the casing can be placed in the body before the lid is joined to enclose the casing within the holder. The lid can then be removed to facilitate removal of the casing after filling. The fill tube may be shaped and sized to fit snugly within the inlet of the holder.

As noted above, the fill material may comprise any known bone-grafting particles including DBM from cancellous or cortical bone and bioceramic materials. In certain embodiments, fill material may include calcium phosphate materials including biphasic calcium phosphate materials with an osteoinductivity-boosting needle-like or nanorod-like surface morphology using hydrothermal and/or chemical processes including exposure to peroxides (e.g., hydrogen peroxide). Other bioceramic fill materials may include monetite, brushite, or MCPM. Additional fill materials may include bioglass, collagen-ceramic mixtures, cell based products, autografts, and growth factor containing products.

Aspects of the invention include an implantable bone graft device comprising a bioresorbable casing comprising both micropores and macropores. The bioresorbable casing may comprise collagen. The collagen casing can contain demineralized bone matrix (DBM) in one or more formats selected from the group consisting of fibers, granules, paste, powder, chips, strips, and sponge. The DBM may be processed from one or more of the group consisting of cortical and cancellous bone. The collagen casing can contain bioceramics in one or more formats selected from the group consisting of fibers, granules, paste, powder, chips, strips, and sponge with or without DBM. In certain embodiments, the bioceramics particles may include HA, tricalcium phosphate, monetite, brushite, or mono-calcium phosphate monohydrate (MCPM). Additional fill materials may include bioglass, collagen-ceramic mixtures, cell based products, autografts, and growth factor containing products.

In various embodiments, the implantable device may include nanopores. The micropores, the macropores, and/or the nanopores may be patterned or random and may be generated through molding or through various mechanical or thermal techniques.

The bioresorbable casing can be closed or may comprise an opening for filling the casing. The bioresorbable casing can be formed by one or more strips of collagen joined together with sutures. The sutures may comprise a bioabsorbable material such as polyglycolic acid, polylactic acid, poly(lactic-co-glycolic acid). In some embodiments, sutures may comprise collagen or any known resorbable or non-resorbable polymer. In certain embodiments, the bioresorbable casing may be formed from a single strip of folded collagen. The bioresorbable casing may be molded in a single piece. The casing may be sized and configured for placement in an anatomical structure of a spine such as in a posterolateral gutter for spinal fusion.

In certain aspects, a bone grafting method is provided that may comprise implanting at a target site an implantable device comprising a bioresorbable casing comprising both micropores and macropores and filled with a fill material comprising one or more of the group consisting of demineralized bone matrix (DBM) and bioceramics. Prior to implanting methods of the invention may include providing an implantable device comprising an open-ended bioresorbable casing comprising both micropores and macropores, filling the open-ended bioresorbable casing with one or more of the group consisting of demineralized bone matrix (DBM) and bioceramics, and closing the open end of the filled bioresorbable casing. The closing step can include suturing the open end of the filled bioresorbable casing at the time of surgery.

Aspects of the invention can include an implantable device kit comprising a holder. The holder may include a body configured for receiving an open-ended bioresorbable casing and sized to accommodate the open-ended bioresorbable casing when filled and an inlet aligned with the body and sized to allow the open-ended bioresorbable casing to pass through the inlet and into the body.

The body may enclose the bioresorbable casing on all sides apart from the inlet. The holder can further include a removable lid that upon removal, providing access to the body for insertion and removal of the open-ended bioresorbable casing. Kits may include a fill tube having a distal end having a cross-sectional profile sized to fit within the open-ended bioresorbable casing and the inlet. The fill tube can include a proximal end having a larger cross-sectional profile than the distal end. The fill tube may have two or more detachably coupled segments.

In certain embodiments, the inlet of the holder and the distal end of the fill tube may be sized such that the distal end of the fill tube can be inserted into the inlet. The inlet of the holder and the distal end of the fill tube can be sized such that the fill tube's outer surface forms a seal with an inner surface of the inlet. Kits may include a plunger sized to fit within the fill tube and operable to force a fill material through the fill tube and into the open-ended bioresorbable casing. The open-ended bioresorbable casing and the fill material may be included in kits of the invention.

In certain aspects, methods of the invention may include making an implantable device by providing a kit as described above with a holder comprising a body configured for receiving an open-ended bioresorbable casing and sized to accommodate the open-ended bioresorbable casing when filled and an inlet aligned with the body and sized to allow the open-ended bioresorbable casing to pass through the inlet and into the body; a fill tube having a distal end having a cross-sectional profile sized to fit within the open-ended bioresorbable casing and the inlet; and a plunger sized to fit within the fill tube. Methods may include coupling an open-ended bioresorbable casing to the fill tube; inserting the open-ended bioresorbable casing through the inlet and into the body of the holder such the fill tube and open-ended bioresorbable casing become held by the holder; and inserting, via the plunger, a fill material through the fill tube and into the open-ended bioresorbable casing to produce a filled open-ended bioresorbable casing.

In certain embodiments, methods may include removing the filled open-opened ended bioresorbable casing from the holder and uncoupling the fill tube from the filled open-opened ended bioresorbable casing. Methods can comprise closing the filled open-ended bioresorbable casing. The body may enclose the bioresorbable casing on all sides apart from the inlet. The holder may further comprise a removable lid that upon removal, providing access to the body for insertion and removal of the open-ended bioresorbable casing. The fill tube can include a distal end having a cross-sectional profile sized to fit within the open-ended bioresorbable casing and the inlet. The fill tube can comprise a proximal end having a larger cross-sectional profile than the distal end.

In certain embodiments, the fill tube may include two or more detachably coupled segments. The inlet of the holder and the distal end of the fill tube may be sized such that the distal end of the fill tube can be inserted into the inlet. The inlet of the holder and the distal end of the fill tube can be sized such that an outer surface of the fill tube forms a seal with an inner surface of the inlet.

BRIEF DESCRIPTION OF THE DRAWINGS

FIG. 1 shows an open-ended bioresorbable casing according to certain embodiments.

FIG. 2 shows an exemplary closed bioresorbable casing.

FIG. 7 shows an exemplary open-ended bioresorbable casing with a fill tube and plunger inserted therein.

FIG. 8 shows an exemplary holder.

DETAILED DESCRIPTION

Systems and methods of the invention relate to bioresorbable casings for providing containment and shape to bone graft particles. Such casings can be preferentially made of collagen or other bio-compatible and/or natural materials. They may be formed of a mesh comprising micro, macro, and/or nanopores. The pores should be sized based on the graft material contained therein to prevent the material from escaping and while allowing osteogenic cells and other biological fluids and materials to pass through, providing access to the graft material. Casings may be provided pre-filled, closed, and ready for use or may be provided open to be filled by a user before use. The open casing may be provided as part of a kit along with fill material and means for filling and closing the casing. Methods of preparing and using casings of the invention are also described herein.

FIGS. 1 and 2 show exemplary bioresorbable casings 101 of the invention. The casing 101 may be made of synthetic materials such as polyesters, polyamides, or polyolefins. Preferred synthetic materials include biodegradable polymers such as polyglycolide (PGA) and poly(lactic-co-glycolic acid) (PLGA). In preferred embodiments, the casing is made of a natural material such as collagen.

Casings preferably have both micropores and macropores. Macropores generally refer to pores between 100 µm to 1000 µm. Micropores generally refer to pores less than about 1 µm to 100 µm and, in certain embodiments, between about 1 µm and about 10 µm. In certain embodiments, the casing material may comprise nanopores, generally referring to pores 1 µm or smaller.

Figure 11:
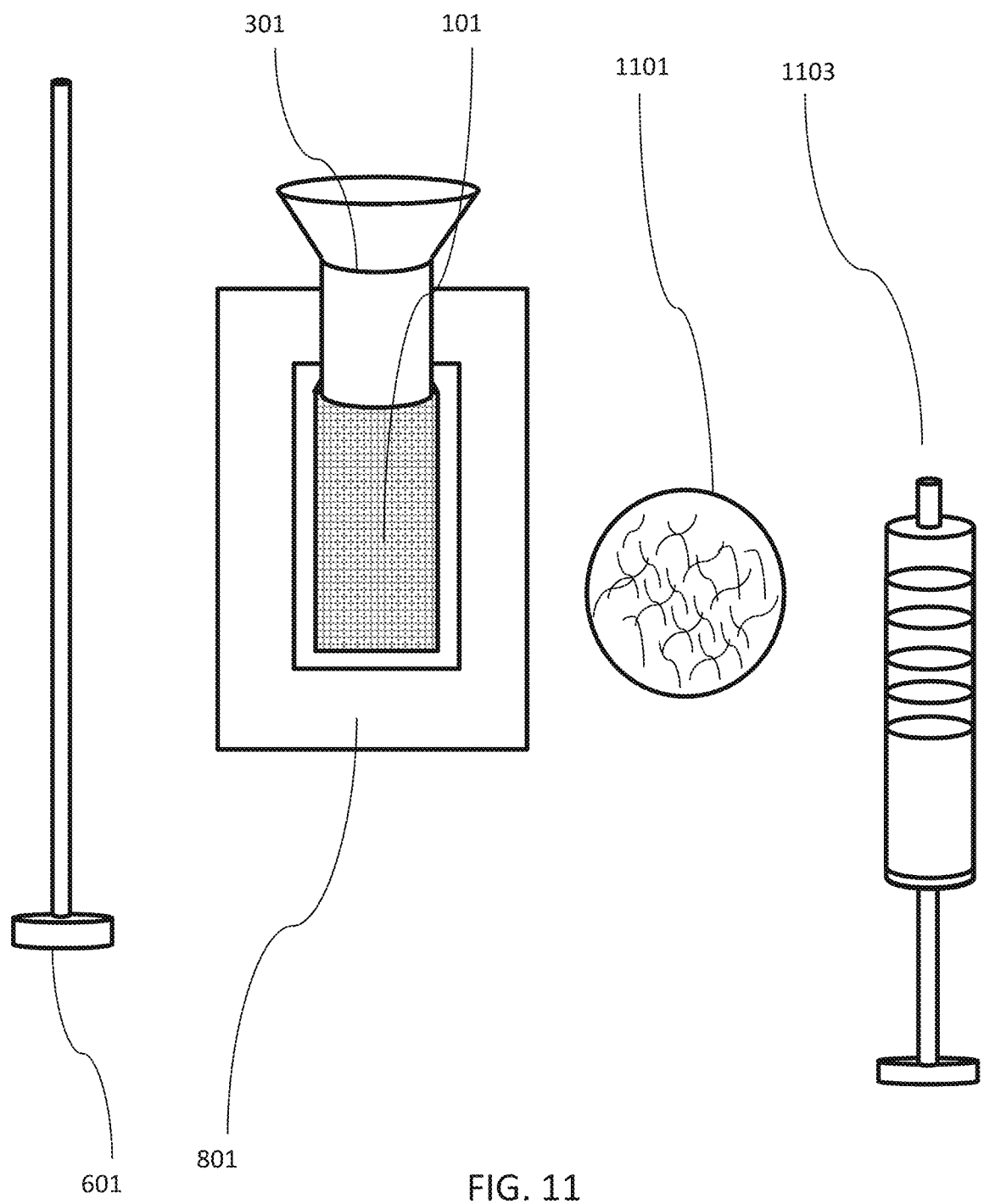
FIG. 11 shows an exemplary kit of the invention.
Figure 12:
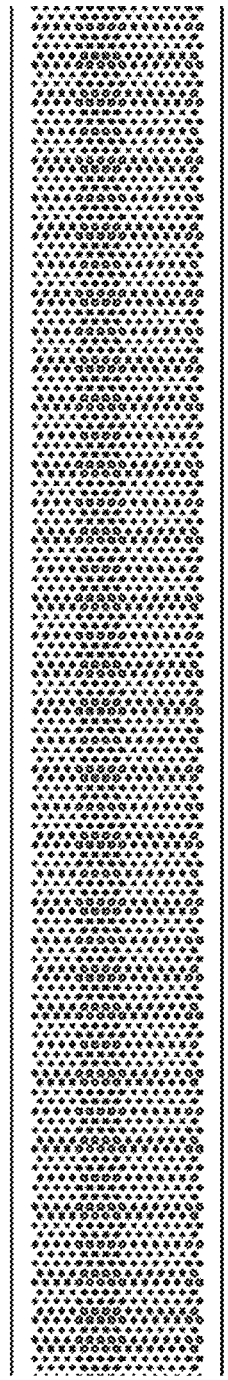
FIG. 12 shows an exemplary collagen strip.

Any of the above pores may be distributed randomly or patterned across the casing's surface. The pores may be distributed in a pattern based on the application of the final implant. For example, the macropores may be concentrated based on the anatomical location of the casing 101 once implanted to provide better access to osteogenic cells, fluids, or other biological material. Micro and macropores may be randomly distributed or patterned based on other considerations. FIG. 11 shows an exemplary collagen strip for use in preparing a casing having an exemplary pattern of pores across the surface of the material.

Pores may be formed via molding of the casing material wherein the size and distribution of the pores are dictated by the surface features of the mold. Casing materials may comprise solid sheets in which pores are created via known mechanical, chemical, or thermal processes. In certain embodiments, laser processing is used to form the desired size and pattern of pores in the casing material. In some embodiments, pores may be punched into the casing.

Casings 101 may be formed into the final desired size and shape through any known technique including injection or other molding techniques. Casings 101 are preferably prepared with a cavity therein to receive and contain the graft material. In initial preparation, an opening 105 should left by which the graft material can be inserted into the casing 101.

The open end 105 may be closed after filling either at a remote manufacturing site or by a user such as a surgeon or other medical professional before implantation using sutures 203 (FIG. 2). Sutures may be any biocompatible material including the natural and synthetic materials used to form the casing 101. In preferred embodiments, the sutures 203 comprise PGA or PLGA or collagen. Sutures may also include non-resorbable materials such as polypropylene and polyethylene. Other sealing methods are contemplated including adhesives, heat, and pressure, depending upon the nature of the casing material and intended use.

In certain embodiments, the casing 101 may be prepared from one or more sheets of the porous casing material. For example a tube-shaped casing 101 may be prepared from two sheets of collagen or other material by laying the sheets together and suturing or otherwise sealing the sides 103 and bottom 107 to form a casing 101 with an opening 105 through which to add graft material. In some embodiments, a single sheet of porous material may be folded along an edge to form the bottom 107 of the casing 101 and then sutured or otherwise joined along the sides 103 to create the open-ended casing 101.

Casings 101 can be prepared and used in any size and shape depending on the intended application. Casing are contemplated for use in medical procedures such as orthopedic surgery and maxillofacial procedures. In certain embodiments, casings of the invention may be sized and shaped for use in spinal fusion procedures. For example casings and implants made therefrom may be configured for placement in a posterolateral gutter for spinal fusion. They may be offered in various sizes depending on the number and position of the vertebrae to be fused and based on the age and/or size of the patient.

Methods of the invention can include obtaining a casing and optionally filling with a graft material if it is not prefilled. Filling may comprise the use of kit components as described below including one or more of a holder, a casing, a fill material, a plunger, and a fill tube. A user may then close the casing if it was not prefilled using the methods described above. Methods can include then implanting the filled casing to repair a bone defect, treat a traumatic injury, perform a spinal fusion, or any other osteogenic treatment calling for a graft prosthesis. Fill material such as those described below, including DBM and/or bioceramics may be obtained in dry form and can be wetted prior to filling. The bioceramics particles may include, for example, HA, tricalcium phosphate, monetite, brushite, or mono-calcium phosphate monohydrate (MCPM). Additional fill materials may include bioglass, collagen-ceramic mixtures, cell based products, autografts, and growth factor containing products.

In certain embodiments, bioresorbable casing may be provided in kit form. Kits may include one or more of a casing, a fill material, a holder, a fill tube, and a plunger to facilitate filling of the casing by a user. Additional materials such as syringes and fluids for wetting and preparing fill material and/or the casing may also be included.

An exemplary kit is shown in FIG. 11. The kit includes a holder 801, a casing 101, and a fill tube 301, all shown assembled ready for filling. A plunger 601 is included as well as fill material 1101 shown in a dish for wetting and preparation as well as a syringe 1103 of fluid for wetting and preparing the fill material 1101.

Figure 3:
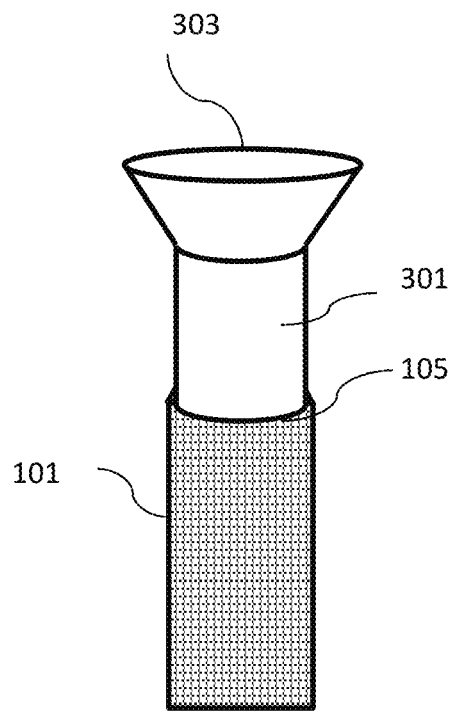
FIG. 3 shows an exemplary open-ended bioresorbable casing with a fill tube inserted therein.
Figure 4:
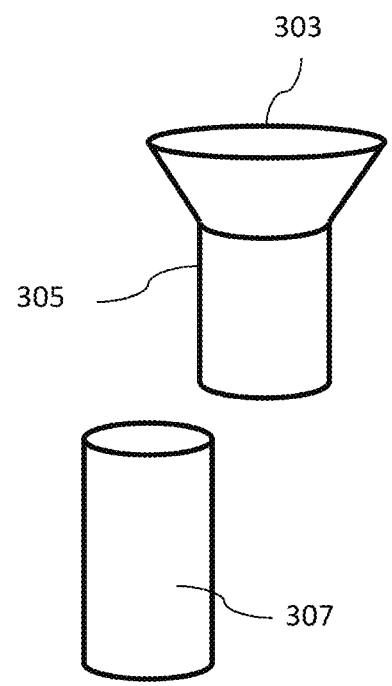
FIG. 4 shows an exemplary two-piece fill tube.
Figure 5:
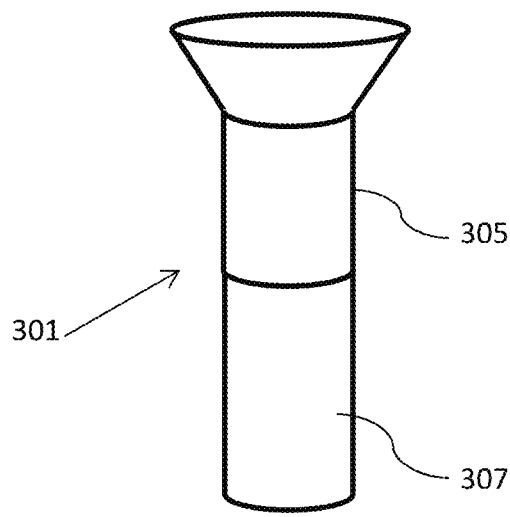
FIG. 5 shows an exemplary assembled fill tube.

A fill tube 301 is depicted in FIGS. 3-5. The fill tube 301 should have at least one end sized to fit within the opening 105 of the casing 101. The tube 301 comprises a lumen through which fill material may be passed into the casing 101 through the opening 105. The casing material may generally offer little material support such that maintaining the opening 105 during filling is difficult. The fill tube 301 can be rigid enough to then maintain the opening 105 for filling. The outer surface of the fill tube 301 is preferably sized to fit snugly within the opening 105 and the inner lumen of the fill tube 301 is preferably sized to allow the passage of fill material therethrough and into the casing 101. The outer surface and lumen of the fill tube 301 may be enlarged at the end not inserted into the opening 105 to ease loading of material. For example, the fill tube 301 may include a funnel 303 at one end providing a large opening for material to be added followed by a gradual reduction in cross-sectional profile to fit within the casing 101. The fill tube 301 may comprise multiple parts to ease in packaging or to provide different funnel 303 options. For example, the fill tube 301 may be made up of two components including a casing insertion portion 307 and a funnel portion 305 which can be assembled prior to filling. Funnel portions 305 of different sizes may be selected based on the fill material.

Figure 6:
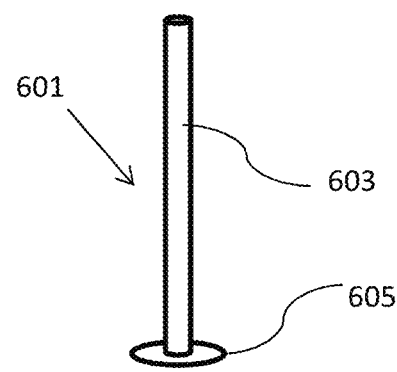
FIG. 6 shows an exemplary plunger.

Fill tubes 301 may be made of any known material including, for example, metal, glass, plastic, and composite materials. In certain embodiments, kits may include a plunger 601 for aiding in casing filling as shown in FIG. 6. The plunger 601 is sized to fit within the lumen of the fill tube as sized at the end inserted into the casing 101. The plunger 601 may have a single size and shape or may have a smaller handle portion 603 and a larger plunging portion 605 to provide a large cross-sectional area for forcing fill material into the casing 101.

The plunger 601 preferably has a cross-sectional profile sized just smaller than the lumen of the fill tube 301 and the opening 105 in the casing 101 so that fill material cannot readily pass between the inside of the fill tube 301 lumen and the edges of the plunger 601. Filling action using the plunger 601 to force fill material through a fill tube 301 into the opening 105 of a casing 101 is shown in FIG. 7. The plunger may include features such as serrations or openings in the plunging portion 605 to physically process the fill material during insertion including separating granules and avoiding clumping.

Kits may include a holder 801 for supporting and positioning a casing 101 for fill. An exemplary holder 801 is shown in FIG. 8. The holder 801 can comprise a body 803 sized to accept the casing 101 and align the opening 105 of the casing 101 with an inlet 805 in the body 803 of the holder 801. As noted above with respect to the fill tube 301, the casing material has little rigidity and, therefore filling the casing 101 can be difficult, even with the use of the fill tube 301. The holder 801 can work alone or in conjunction with the fill tube 301 to support the outside of the casing 101 during fill. The holder 801, like the fill tube 301, and the plunger 601 may be made out of any known material including, for example, metal, glass, plastic, and composite materials. The holder 801 can be operable to fully enclose the casing 101 only providing access to the opening 105 of the casing 101 through an inlet 805 in the holder 801. Accordingly, the holder can assist in maintaining sterility of the casing 101 and minimizing the potential for damage through repeated handling of the casing 101 directly.

Figure 9:
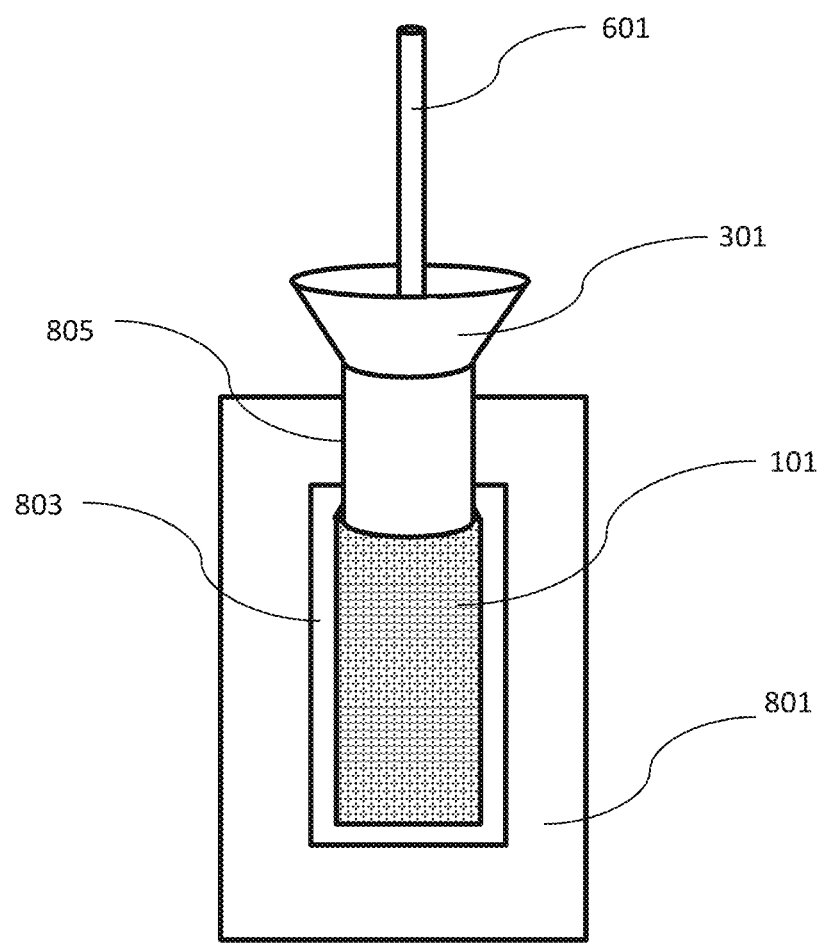
FIG. 9 shows an open-ended bioresorbable casing in a body of an exemplary holder.

A casing 101 inserted into the body 803 of a holder 801 is depicted in FIG. 9. The body 803 and the casing 101 are similarly sized and shaped to aid in positioning of the casing opening 105 and the holder inlet 805. The holder inlet 805 may also be sized and shaped along with the fill tube 301 such that the fill tube can be passed through the inlet 805 into the casing 101 within the body 803. The components can be sized such that the outer surface of the fill tube 301 contacts the inner edges of the inlet 805 and may even form a seal, protecting the outside of the casing 101 such that the lumen of the fill tube 301 provides the only access and point of exposure to the casing 101.

Figure 10:
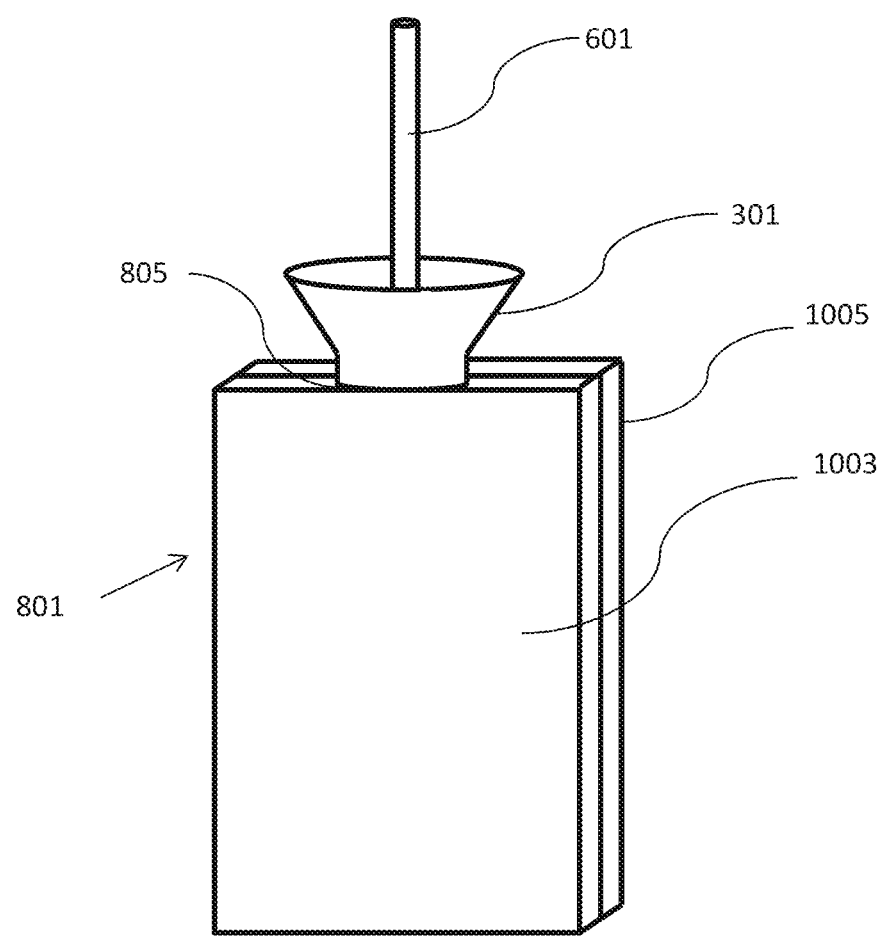
FIG. 10 shows an open-ended bioresorbable casing enclosed in an exemplary holder.

In order to facilitate casing 101 placement in and retrieval from the body 803 of the holder 801, the holder may comprise multiple components including a lid 1003 as shown in FIG. 10. At least a portion of the body 803 may be formed in a base 1005 of the holder 801 such that the casing 101 can be positioned therein. The fill tube 301 may be inserted into the opening 105 of the casing 101 before or after the casing 101 is placed in the body 803. Once positioned, the lid 1003 or other component of the holder 801 may then be coupled to the base 1005 to form the complete, enclosed body 803 and inlet 805 of the holder 801 with the casing inside. Once filled, the lid 1003 may be removed and the filled casing 101 can be taken from the body 803, closed, and implanted.

In various embodiments, casing disclosed herein may be pre-filled with a bone-grafting material. Preferably the material is provided in particulate form to provide increased surface area for infiltration by host cells and osteogenesis. Materials may include bone material which may be obtained from the patient before or during the implantation procedure. In certain embodiments, DBM may be used to fill the casing. DBM is bone that has had the inorganic mineral removed, leaving behind the organic matrix. Removal of the bone mineral exposes more biologically active bone morphogenetic proteins which aid in bone and cartilage formation. DBM is more biologically active than standard bone grafts but the mechanical properties of the bone are lost. Accordingly, casings of the invention are particularly useful in containing DBM and providing the mechanical support and shape desired for particular bone graft prostheses. Any combination of graft materials may be provided in the form of fibers, granules, paste, powder, chips, strips, sponge, or any other available particle type and any combination of these particle types.

In various embodiments, fill material may comprise metals, like titanium or tantalum, polymers like polylactides, hydrogel-based materials, or bioceramics. Bioceramics may include biphasic calcium phosphate which may be processed to produce osteoinductive surface morphologies as described below. Additional osteoinductive fill materials as well as prosthesis applications are described in U.S. Pat. Nos. 9,364,583; 4,430,760; and 9,801,978, incorporated by reference herein. Fill material may include bioglass, collagen-ceramic mixtures, as well as cell based products and growth factor containing products. See V. Krishnan and T. Lakshmi, 2013, Bioglass: A novel biocompatible innovation, J Adv Pharm Technol Res. 4(2): 78-83. Example of materials and agents which may be added to a fill material in a casing of the invention include, for example, osteogenic or chondrogenic proteins or peptides; DBM powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

Fill materials may include biphasic calcium phosphate with modified surface morphologies prepared using hydrothermal and/or chemical treatment such as those described, for example, in U.S. patent application Ser. No. 16/828,583.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. An implantable bone graft device comprising a bioresorbable casing comprising a cavity for receiving and containing a fill material and a surface having both micropores and macropores, wherein the macropores are created in a sheet of bioresorbable material by mechanical, chemical, or thermal process and patterned and sized to prevent the fill material within the cavity from escaping therethrough while allowing osteogenic cells to pass through.

2. The implantable device of claim 1 wherein the bioresorbable casing comprises collagen.

3. The implantable device of claim 2 wherein the collagen casing contains demineralized bone matrix (DBM) in one or more formats selected from the group consisting of fibers, granules, paste, powder, chips, strips, and sponge.

4. The implantable device of claim 3 wherein the DBM is processed from one or more of the group consisting of cortical and cancellous bone.

5. The implantable device of claim 2 wherein the collagen casing contains bioceramics in one or more formats selected from the group consisting of fibers, granules, paste, powder, chips, strips, and sponge.

6. The implantable device of claim 2 wherein the collagen casing contains demineralized bone matrix (DBM) and bioceramics.

7. The implantable device of claim 1 wherein the micropores are random.

8. The implantable device of claim 1 wherein the macropores are generated through molding.

9. The implantable device of claim 1 wherein the macropores are generated through mechanical or thermal techniques.

10. The implantable device of claim 1 wherein the bioresorbable casing is closed.

11. The implantable device of claim 1 wherein the bioresorbable casing comprises an opening for filling the casing.

12. The implantable device of claim 2 wherein the bioresorbable casing is formed by one or more strips of collagen joined together with sutures.

13. The implantable device of claim 12 wherein the sutures comprise a bioabsorbable material selected from the group consisting of polyglycolic acid, polylactic acid, and poly(lactic-co-glycolic acid).

14. The implantable device of claim 12 wherein the bioresorbable casing is formed from a single strip of folded collagen.

15. The implantable device of claim 1 wherein the bioresorbable casing is molded in a single piece.

16. The implantable device of claim 1 sized and configured for placement in an anatomical structure of a spine.

17. The implantable device of claim 16 sized and configured for placement in a posterolateral gutter for spinal fusion.

18. A bone grafting method comprising: implanting at a target site an implantable device comprising a bioresorbable casing comprising:
   a surface having both micropores and macropores created in a sheet of bioresorbable material by mechanical, chemical, or thermal process; and a cavity filled with a fill material comprising one or more of the group consisting of demineralized bone matrix (DBM) and bioceramics, wherein the macropores are patterned and sized to prevent the fill material from escaping therethrough while allowing osteogenic cells to pass through.

19. The bone grafting method of claim 18, wherein prior to implanting, the method further comprises:
providing an implantable device comprising an open-ended bioresorbable casing comprising both micropores and macropores;
filling the open-ended bioresorbable casing with one or more of the group consisting of demineralized bone matrix (DBM) and bioceramics; and
closing the open end of the filled bioresorbable casing.

20. The method of claim 19 wherein the closing step comprises suturing the open end of the filled bioresorbable casing.

21. The bone grafting method of claim 18 wherein the target site comprises an anatomical structure of a spine.

22. The method of claim 18 wherein the DBM matrix is in one or more formats selected from the group consisting of fibers, granules, paste, powder, chips, strips, and sponge.

23. The method of claim 18 wherein the DBM matrix is processed from one or more of the group consisting of cortical and cancellous bone.

24. The method of claim 18 wherein the bioceramics comprise one or more formats selected from the group consisting of fibers, granules, paste, powder, chips, strips, and sponge.

* * * * *